United States Patent
Akinwande et al.

(10) Patent No.: US 10,175,187 B2
(45) Date of Patent: Jan. 8, 2019

(54) INTEGRATION OF MONOLAYER GRAPHENE WITH A SEMICONDUCTOR DEVICE

(71) Applicant: Board of Regents, The University of Texas System, Austin, TX (US)

(72) Inventors: Deji Akinwande, Austin, TX (US); Seyedeh Maryam Mortazavi Zanjani, Austin, TX (US); Mir Mohammad Sadeghi, Austin, TX (US); Milo Holt, Pflugerville, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/609,706

(22) Filed: May 31, 2017

(65) Prior Publication Data
US 2017/0350835 A1 Dec. 7, 2017

Related U.S. Application Data

(60) Provisional application No. 62/346,744, filed on Jun. 7, 2016.

(51) Int. Cl.
| | |
|---|---|
| *H03K 3/03* | (2006.01) |
| *G01N 27/12* | (2006.01) |
| *H01L 29/16* | (2006.01) |
| *G01N 27/02* | (2006.01) |
| *G01N 33/00* | (2006.01) |

(52) U.S. Cl.
CPC ......... *G01N 27/02* (2013.01); *G01N 33/0027* (2013.01); *H03K 3/0315* (2013.01); *G01N 27/127* (2013.01)

(58) Field of Classification Search
CPC ............. G01N 27/045; G01N 27/4148; G01N 27/127; G01N 27/128; G01N 27/129; H03K 3/0315

USPC ................. 324/633; 331/57; 438/49; 257/27
See application file for complete search history.

(56) References Cited

U.S. PATENT DOCUMENTS

| | | | |
|---|---|---|---|
| 8,703,558 B2 | 4/2014 | Liang et al. | |
| 9,029,836 B2 | 5/2015 | Park et al. | |
| 2011/0210314 A1* | 9/2011 | Chung | ............... H01L 29/1606 257/29 |
| 2011/0227043 A1 | 9/2011 | Guo et al. | |
| 2013/0082235 A1* | 4/2013 | Gu | ..................... H01L 21/8258 257/9 |
| 2014/0306184 A1* | 10/2014 | Ruhl | .................. H01L 29/1606 257/29 |
| 2015/0303871 A1 | 10/2015 | Jenkins et al. | |

(Continued)

OTHER PUBLICATIONS

Chen et al., Fully Integrated Graphene and Carbon Nanotube Interconnects for Gigahertz High-Speed CMOS Electronics, IEEE Transactions on Electron Devices, vol. 57, No. 11, Nov. 2010.*

(Continued)

*Primary Examiner* — Didarul Mazumder
(74) *Attorney, Agent, or Firm* — Baker Botts L.L.P.

(57) ABSTRACT

The integration of monolayer graphene with a semiconductor device for gas sensing applications involves obtaining a CMOS device that is prepared to receive monolayer graphene channels. After population of the monolayer graphene channels on the CMOS device, electrical contacts are formed at each end of the monolayer graphene channels with interconnect vias having sidewalls angled at less then 90°. Additional metallization pads are added at the location of the monolayer graphene channels to improve planarity and reliability of the semiconductor processing involved.

14 Claims, 10 Drawing Sheets
(10 of 10 Drawing Sheet(s) Filed in Color)

(56) References Cited

U.S. PATENT DOCUMENTS

2015/0372159 A1  12/2015  Englund et al.
2016/0377566 A1*  12/2016  Han .................... H03K 3/0315
                                                      324/633

OTHER PUBLICATIONS

Mortazavi Zanjani, Seyedeh Maryam. "Heterogeneous integration of graphene and Si CMOS for gas sensing applications." Diss. 2014; 130 pages, 2014.
Chen, Xiangyu, et al. "Fully integrated graphene and carbon nanotube interconnects for gigahertz high-speed CMOS electronics." IEEE Transactions on Electron Devices 57.11 (2010): 3137-3143; 7 page, 2010.
Lee, Kyeong-Jae, et al. "Low-swing signaling on monolithically integrated global graphene interconnects." IEEE Transactions on Electron Devices 57.12 (2010): 3418-3425; 8 pages, 2010.
Lee, Kyeong-Jae, et al. "Demonstration of a subthreshold FPGA using monolithically integrated graphene interconnects." IEEE Transactions on Electron Devices 60.1 (2013): 383-390; 8 pages, 2013.
International Search Report and Written Opinion received for PCT Patent Application No. PCT/US2017/035197, dated Aug. 25, 2017; 10 pages.
Mortazavi Zanjani, Seyedeh Maryam, et al. "Enhanced sensitivity of graphene ammonia gas sensors using molecular doping." Applied Physics Letters 108.3 (2016); 5 pages, 2016.
Zanjani, Seyedeh Maryam Mortazavi, et al. "3D integrated monolayer graphene-Si CMOS RF gas sensor platform." *npj 2D Materials and Applications* 1.1 (2017): 36; 9 pages, 2017.

\* cited by examiner

INTEGRATION OF MONOLAYER GRAPHENE WITH A SEMICONDUCTOR DEVICE

RELATED APPLICATIONS

This application claims priority to U.S. Provisional Application Ser. No. 62/346,744 filed Jun. 7, 2016, and which is incorporated herein by reference in its entirety.

BACKGROUND

Field of the Disclosure

This disclosure relates generally to semiconductor devices and, more particularly, to integration of monolayer graphene with a semiconductor device for gas sensing applications.

Description of the Related Art

Detecting presence of gas molecules is important for controlling chemical processes, safety systems, and industrial and medical applications. Despite progress in developing and improving various types of gas sensors, sensors with higher sensitivity, selectivity, lower sensing limit, and lower cost that can perform at room temperature remain desirable. Graphene is a promising candidate for gas sensing applications due to its unique transport properties, exceptionally high surface-to-volume ratio, and low electrical noise.

BRIEF DESCRIPTION OF THE DRAWINGS

A more complete understanding of the present embodiments and advantages thereof may be acquired by referring to the following description taken in conjunction with the accompanying drawings, which relate to embodiments of the present disclosure. The patent or application file contains at least one drawing executed in color. Copies of this patent or patent application publication with color drawings will be provided by the Office upon request and payment of the necessary fee.

DESCRIPTION OF PARTICULAR EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

As noted previously, gas sensors of increasingly greater sensitivity, faster response time and portability are desired for many industrial applications. Furthermore, a gas sensor that is coupled with back-end complimentary metal-oxide semiconductor (CMOS) amplification and analysis circuitry also provides advantages from tighter system integration, which may improve functionality and may lower power consumption and cost. In general, integration of gas sensors with semiconductor devices enables industrial scale manufacturing at low cost, which is advantageous for many applications.

Current electrochemical sensors may provide suitable response times for certain applications, but may have inherently limited response time due to diffusion processes through an electrolyte. Furthermore, solid state metal oxide semiconductor (MOS) sensors may suffer from high internal resistance, and may be operational at high temperatures to activate the MOS surface. Oxygen from the air may bind to the surface at high temperatures (usually >400 C) to form an active sensing layer at the MOS surface, while the sensing mechanism of MOS sensors may be a redox reaction between the gas analyte and the MOS surface. As a result, MOS sensors may be difficult to integrate in a low-power CMOS package.

The discovery of graphene and the subsequent progress in nanotechnology and nanomaterials have led to ultra-sensitive room-temperature sensors that can detect individual analyte molecules, such as nitrogen dioxide ($NO_2$). Certain key factors of graphene as a sensor material include unique transport properties, extremely high surface-to-volume ratio, and low electrical noise. Electronic states of graphene may be affected by adsorbed gas molecules and the charge transfer between graphene and the adsorbed gas molecules can modify carrier concentration without altering mobility.

As will be described in further detail, the inventors of the present disclosure have integrated monolayer graphene with a semiconductor device for gas sensing applications. The monolayer graphene integrated with a semiconductor device disclosed herein is compatible with CMOS technology, which is desirable for industrial scale low-power implementation. The monolayer graphene integrated with a semiconductor device disclosed herein is compatible with various semiconductor technologies and substrates. The monolayer graphene integrated with a semiconductor device disclosed herein may be fabricated with relatively few post-CMOS processing steps for relatively simple and low cost fabrication.

Figure 1:
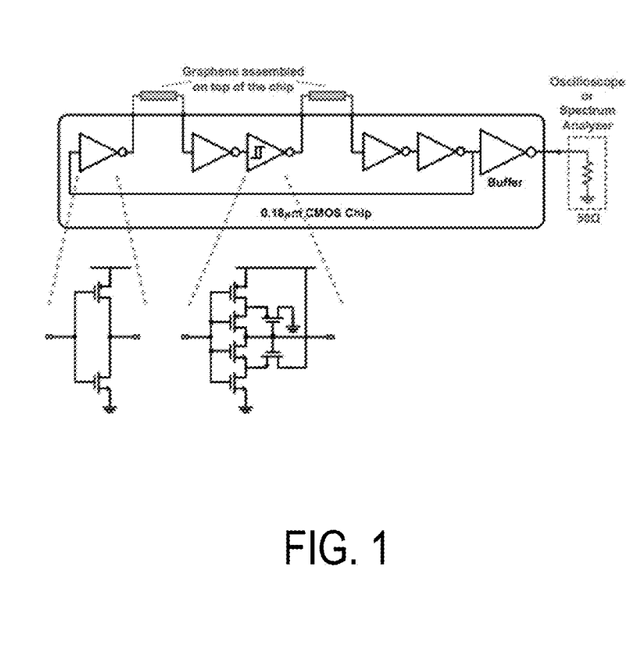
FIG. 1 illustrates selected elements of an example of a ring oscillator circuit comprising monolayer graphene.

Turning now to the drawings, FIG. 1 illustrates selected elements of an example of a ring oscillator circuit comprising monolayer graphene for gas sensing applications. It is noted that FIG. 1 is not drawn to scale and is a schematic illustration. As shown in FIG. 1, the ring oscillator circuit is a 5-stage oscillator that may be implemented in a CMOS semiconductor. Using the ring oscillator circuit, small changes in the electronic properties of the monolayer graphene, such as resistivity, under exposure to analyte gases, such as nitrogen dioxide (NO$_2$), may be detected and measured.

As will be described in further detail below, the monolayer graphene is introduced onto a top surface of a CMOS semiconductor device that has been prepared with the ring oscillator circuit and with interconnect vias that bridge the stages of the oscillator. The monolayer graphene is formed on the top surface of the CMOS semiconductor device and connected using metal layer deposition to the interconnect vias formed through a passivation layer otherwise covering the CMOS semiconductor device.

Figure 2:
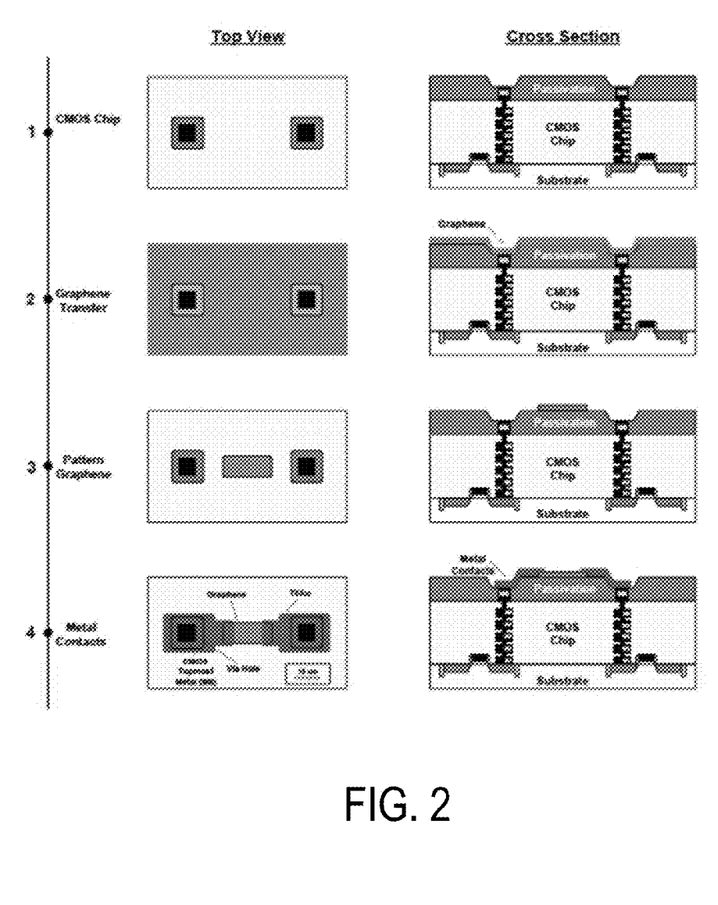
FIG. 2 schematically illustrates an overview of the process for integrating monolayer graphene with a semiconductor device.

Referring now to FIG. 2, an overview of the process for integrating monolayer graphene with a semiconductor device is schematically illustrated. It is noted that FIG. 2 is not drawing to scale. In FIG. 2, four (4) steps are shown of the semiconductor device with a top view on the left side and a corresponding cross-sectional view on the right side.

In step 1 at the top of FIG. 2, a CMOS device (shown as a CMOS Chip) is provided. The CMOS device may be externally fabricated for subsequent integration of the monolayer graphene. The CMOS device may include the ring oscillator circuit shown in FIG. 1. In various embodiments, the CMOS device may be fabricated with various functionality, such as for gas sensing applications, including, but not limited to, sensor activation, sensor passivation, sensor power, sensor interconnects, signal conditioning, signal amplification, digital signal processing, and signal output, among other functions. As shown in FIG. 2 at step 1, a single monolayer graphene interconnect is shown with two vias through the passivation layer. In the cross-section view on the right side, the different metallization layers of the CMOS device are represented as black blocks and are labeled M1, M2, M3, M4, M5, and M6 in sequential order from an underlying substrate towards the passivation layer. It is noted that various elements in the CMOS device are not shown in FIG. 2 for descriptive clarity. The contacts for the monolayer graphene are provided in the M6 metallization layer of the CMOS device, which are exposed by the interconnect vias. It is noted that the CMOS device shown in step 1 of FIG. 2 may be externally fabricated for subsequent integration with monolayer graphene, as disclosed herein, which may be economically and logistically desirable. It is further noted that sidewalls of the interconnect vias are purposefully designed with a lower angle than 90 degrees to promote reliable contact of the monolayer graphene with the M6 contacts (see also step 4, FIG. 2).

As shown in step 2 in FIG. 2, monolayer graphene is transferred to the entire surface of the CMOS device. The graphene in FIG. 2 step 2 was synthesized via chemical vapor deposition (CVD). The CVD graphene was then transferred to the surface of the CMOS device as shown. The thickness and quality of graphene samples was evaluated with Raman spectroscopy (see also FIGS. 5B and 5C), using a neodymium-doped yttrium aluminum garnet (Nd:YAG) laser at 532 nm wavelength under ambient conditions.

Then, as shown in FIG. 2, step 3, monolayer graphene channels on the surface of the CMOS chip were patterned using electron beam lithography and etched using a low-power reactive-ion-etch process in oxygen plasma. The monolayer graphene channels were formed over the passivation layer for a plurality of interconnect vias prepared on the CMOS device.

As shown in step 4 in FIG. 2, electrical contacts to the monolayer graphene channel were made using electron beam lithography followed by deposition of titanium Ti (5 nm)/gold Au (45 nm) using e-beam evaporation and a lift-off process. Each electrical contact spanned from one end of the monolayer graphene channel to the M6 contact in an adjacent interconnect via. The electrical contacts comprising Ti/Au were approximately 50 nm thick. In this manner, the monolayer graphene was integrated into the functional ring oscillator circuit depicted in FIG. 1.

As illustrated in FIG. 2, the post-CMOS processing steps involved in the integrated monolayer graphene semiconductor device disclosed herein are relatively simple, which is advantageous. Table 1 below compares the post-CMOS processing steps in the integrated monolayer graphene semiconductor device disclosed herein with three published prior art references disclosing graphene integration into semiconductor devices. In Table 1, Reference 1 is X. Y. Chen, D. Akinwande, K. J. Lee, G. F. Close, S. Yasuda, B. C. Paul, S. Fujita, J. Kong, and H. S. P. Wong, "Fully Integrated Graphene and Carbon Nanotube Interconnects for Gigahertz High-Speed CMOS Electronics," IEEE Transactions on Electron Devices, vol. 57, pp. 3137-3143, November 2010; Reference2 is K. J. Lee, M. Qazi, J. Kong, and A. P. Chandrakasan, "Low-Swing Signaling on Monolithically Integrated Global Graphene Interconnects," IEEE Transactions on Electron Devices, vol. 57, pp. 3418-3425, December 2010; and Reference3 is K. J. Lee, H. Park, J. Kong, and A. P. Chandrakasan, "Demonstration of a Subthreshold FPGA Using Monolithically Integrated Graphene Interconnects," IEEE Transactions on Electron Devices, vol. 60, pp. 383-390, January 2013. As evident from Table 1, the methods and operations disclosed herein for forming the integrated monolayer graphene semiconductor device are reduced in scope and complexity compared to the published references, which is desirable and economically beneficial.

TABLE 1

Comparison of methods to integrate graphene into a semiconductor device.

| Disclosed herein | Prior Art Reference1 | Prior Art Reference2 | Prior Art Reference3 |
|---|---|---|---|
| a) Transfer and pattern of monolayer graphene; and b) Deposit Ti/Au electrical contacts. | a) Transfer and pattern of graphene; b) Deposit Cr/Au contacts; c) Etch via holes through passivation layer; and d) Deposit Ti contact to establish electrical connection. | a) Transfer and pattern of graphene; b) Deposit Ti/Pt contacts; c) Etch via holes through passivation layer; and d) Deposit via plug. | a) Etch via holes through passivation layer; b) Deposit via plug; c) Transfer and pattern of graphene; and d) Deposit contacts. |

Figure 3:
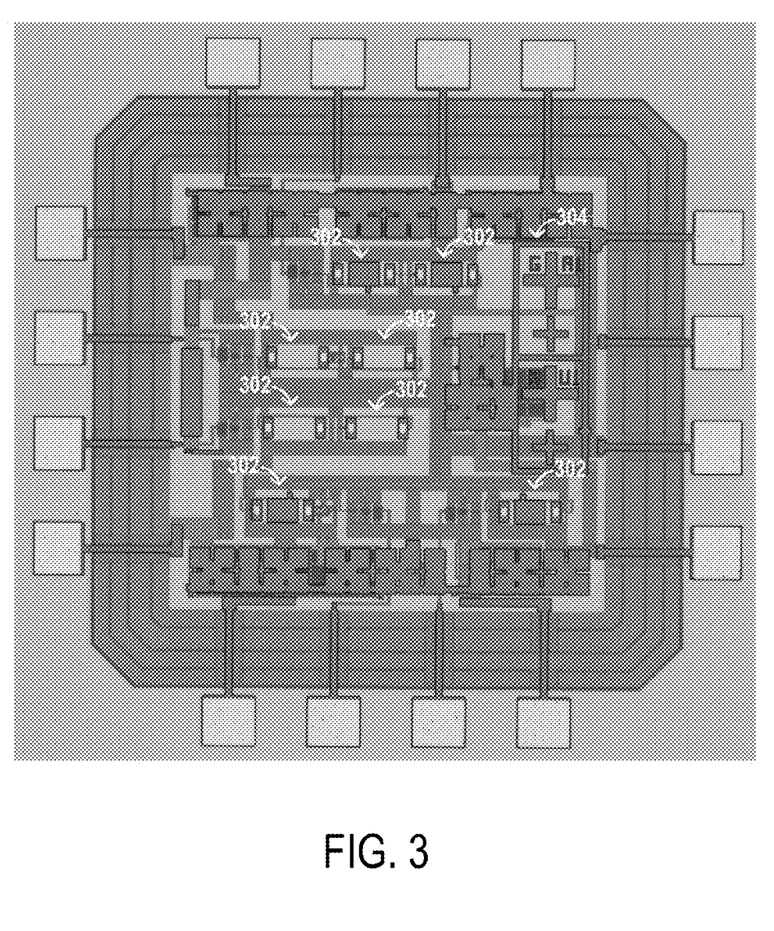
FIG. 3 is a micrograph image of the CMOS device prior to transfer and integration of monolayer graphene with a CMOS device.

Referring now to FIG. 3, a micrograph image of the CMOS device prior to monolayer graphene deposition is shown. The image in FIG. 3 accordingly corresponds to the state of the CMOS device depicted in FIG. 2 step 1. For example, the CMOS device depicted in FIG. 3 may be in the state delivered by a supplier. Visible in FIG. 3 are locations 302 corresponding to individual monolayer graphene channels. The locations 302 each have two interconnect vias on either side for the electrical contacts to the monolayer graphene that are subsequently deposited, as described above with respect to FIG. 2. Also visible in FIG. 3 are alignment marks 304, which may be used for various patterning and transfer steps.

Figure 4A:
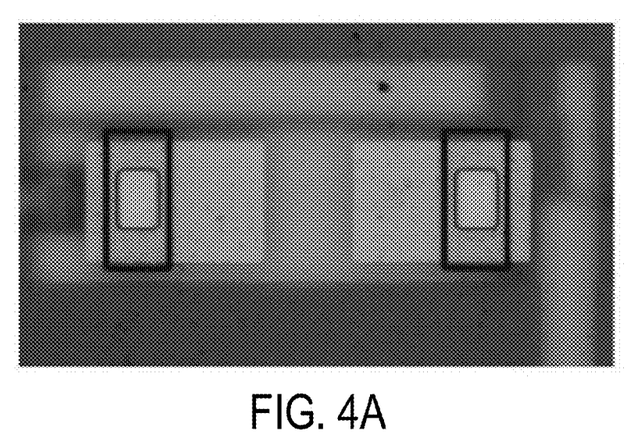
FIGS. 4A, 4B, and 4C are depictions of magnified views of a single monolayer graphene channel.
Figure 4B:
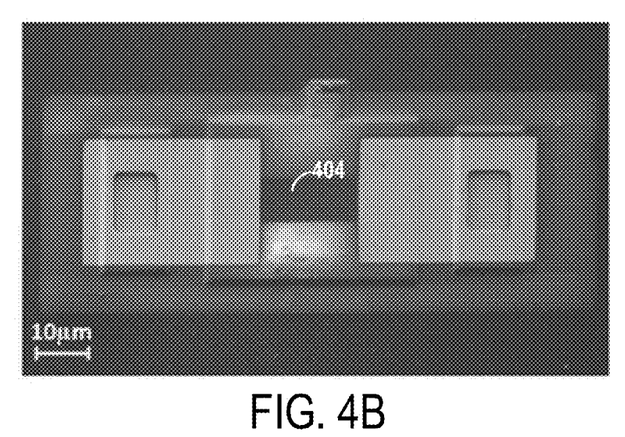
Figure 4C:
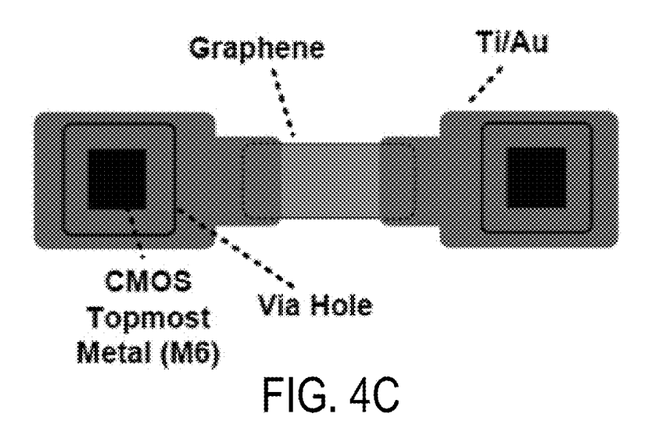

Referring now to FIGS. 4A, 4B, and 4C, magnified views of a single monolayer graphene channel connected to the interconnect vias at each end are shown. FIG. 4A is a microscope image using visible light that shows a magnified view of a monolayer graphene channel corresponding to location 302 in FIG. 3. Because FIG. 4A is taken using visible light, the monolayer graphene channel is not visible, but the electrical contacts to the interconnect vias are visible. FIG. 4B is a scanning electron microscope (SEM) image of the same monolayer graphene channel shown in FIG. 4A. In FIG. 4B, a monolayer graphene channel 404 is visible as a dark region between the interconnect vias. FIG. 4C is a schematic illustration of the same monolayer graphene channel shown in FIGS. 4A and 4B, illustrating the layout of the M6 metallization layer pad in the interconnect via, the Ti/Au electrical contacts, and the monolayer graphene channel.

Figure 5A:
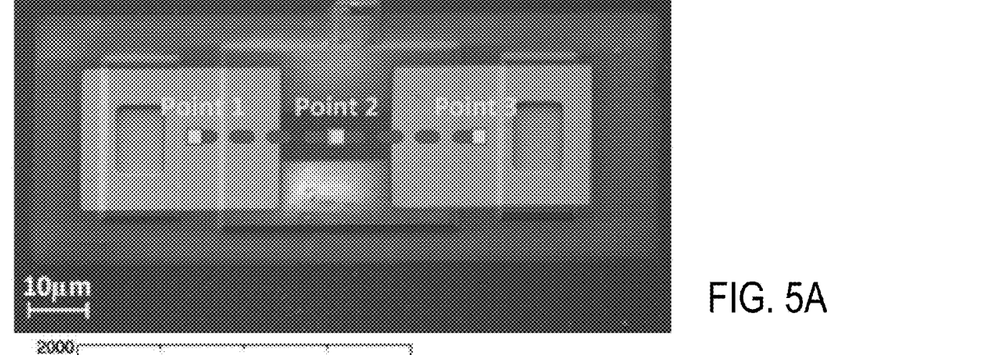
FIGS. 5A, 5B, and 5C illustrate results for Raman spectroscopy of a single monolayer graphene channel.
Figures 5B, 5C:
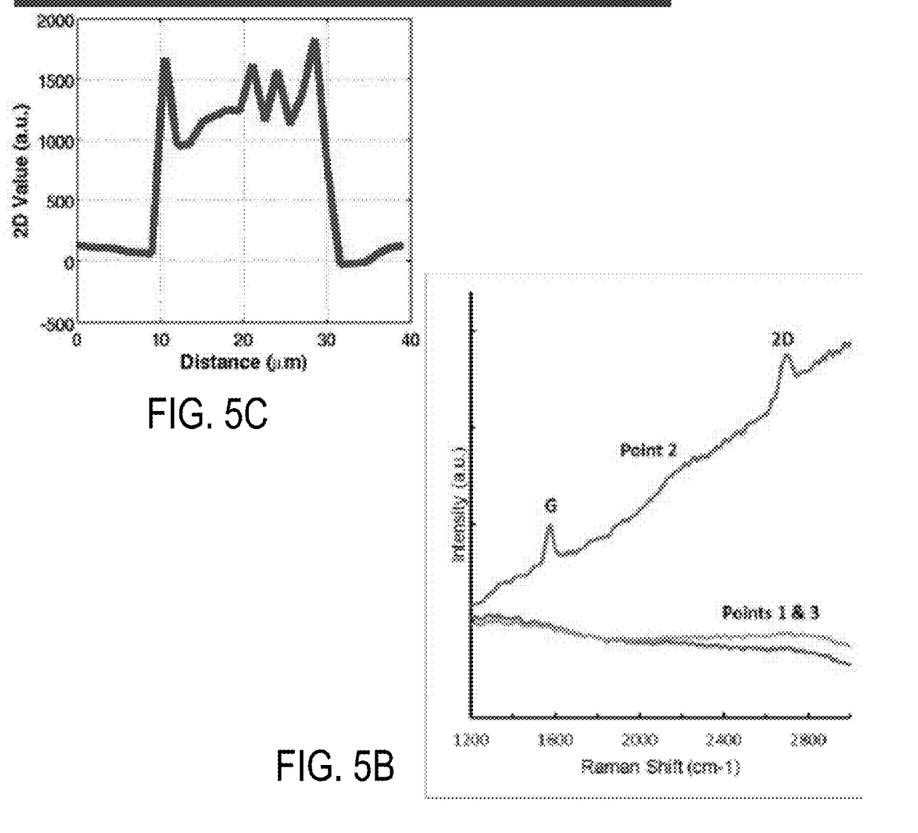

Referring now to FIGS. 5A, 5B, and 5C, results for Raman spectroscopy at three distinct points of a single monolayer graphene channel are illustrated. In FIG. 5A, the SEM micrograph of FIG. 4B is shown with the three points along a line extending from one interconnect via to the other spanning across the monolayer graphene channel. A first point (Point 1) and a third point (Point 3) are located at the Ti/Au electrical contacts to the M6 metallization layer formed over the interconnect vias. A second point (Point 2) is located at the monolayer graphene channel. In FIG. 5B, Raman spectroscopy results of each of the three points described in FIG. 5A are shown. The Raman spectra at the first point and at the third point do not show any graphene peaks. The Raman spectra at the second point shows G and 2D peaks that are characteristic of graphene. FIG. 5C shows the 2D peak intensity along the line shown in FIG. 5A, and illustrates the continuity of graphene across the channel. The Raman spectra at the second point showed a symmetric 2D peak with full width at half maximum (FWHM) of about 28 $cm^{-1}$, a 2D peak to G peak intensity ratio (I(2D)/I(G)) greater than about 3, and a negligible ratio of D peak to G peak intensity (I(D)/I(G)), which is indicative of high quality monolayer graphene.

Figure 6:
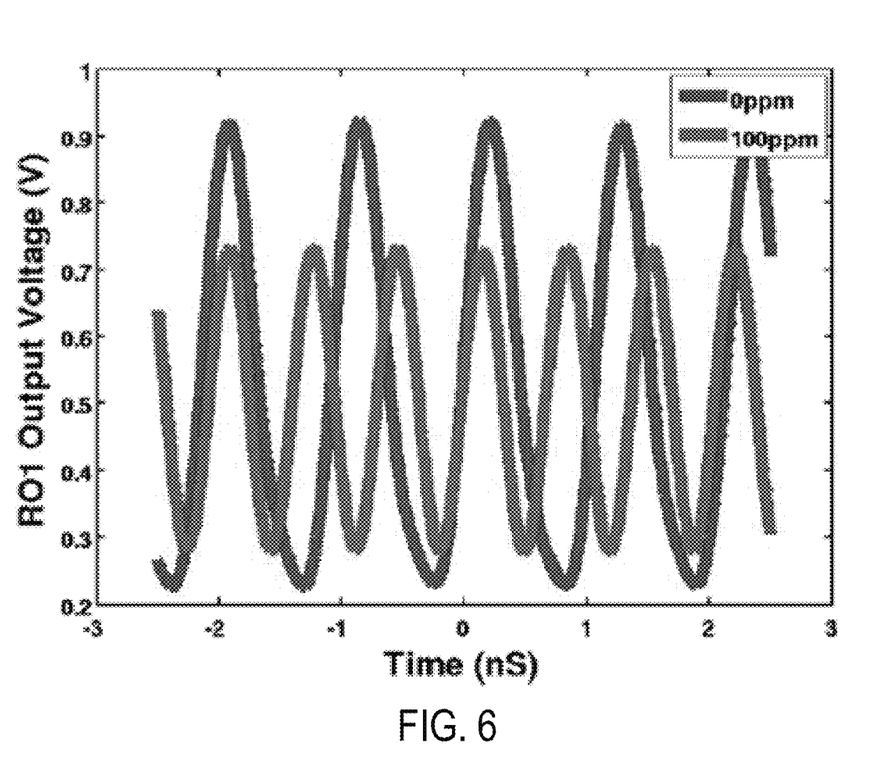
FIG. 6 illustrates signal plots showing a frequency response of the CMOS device after transfer and electrical connection of the monolayer graphene channels with a CMOS ring oscillator.

Referring now to FIG. 6, signal plots showing a frequency response of the CMOS device after monolayer graphene transfer and electrical connection of the monolayer graphene channels are shown. The signal plots shown in FIG. 6 are outputs of the ring oscillator circuit shown in FIG. 1, which begins to generate an oscillating output when power is applied. In FIG. 6, the blue plot shows a base output frequency without exposure to an analyte gas, corresponding to 0 ppm. In FIG. 6, the red plot shows a frequency shift under exposure to 100 ppm $NO_2$ flow in dry air. At the gas sources, concentration of $NO_2$ gas was 100 parts per million (ppm) in dry air. During measurements, the gas concentration in the measurement chamber was controlled using mass flow controllers (MFCs) ahead of a mixing manifold, with $N_2$ as a diluting gas. In the case of FIG. 6, no $N_2$ dilution gas was flowed. The measurements described herein were carried out at a constant flow of gas at 500 Torr pressure and at room temperature. The observation of a frequency shift under exposure to $NO_2$ verifies that the ring oscillator circuit device has been properly constructed within the delivered CMOS device, the monolayer graphene has been successfully integrated with the CMOS device, and the device is functioning as a sensor.

Figure 7:
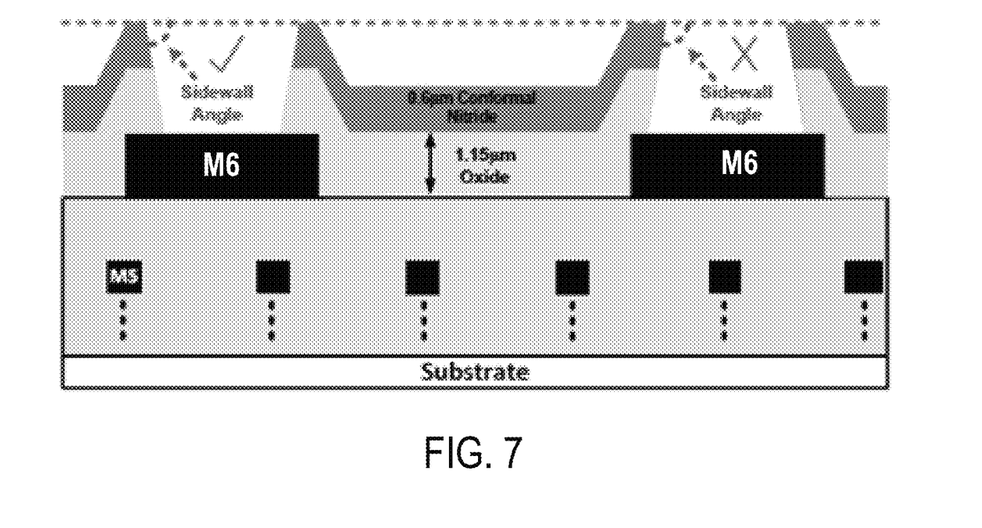
FIG. 7 illustrates a cross-sectional schematic view of interconnect vias.

Referring now to FIG. 7, a cross-sectional schematic illustration of the interconnect vias is shown. Specifically, on the left side, FIG. 7 illustrates that the side walls of the interconnect via have been etched to have an angle less than 90°, which was found to be beneficial in forming the electrical connections to the monolayer graphene channel. A sidewall angle of less than 90° improves the contact reliability between the monolayer graphene and the M6 metallization layer during the subsequent Ti/Au metal deposition, as described above. The inclined sidewall angle of less than 90° may be formed by the supplier of the CMOS device prior to integration of the monolayer graphene channels. Also shown in the right side of FIG. 7 is an undesirable implementation of the interconnect vias having a sidewall angle of greater than 90°.

Figure 8:
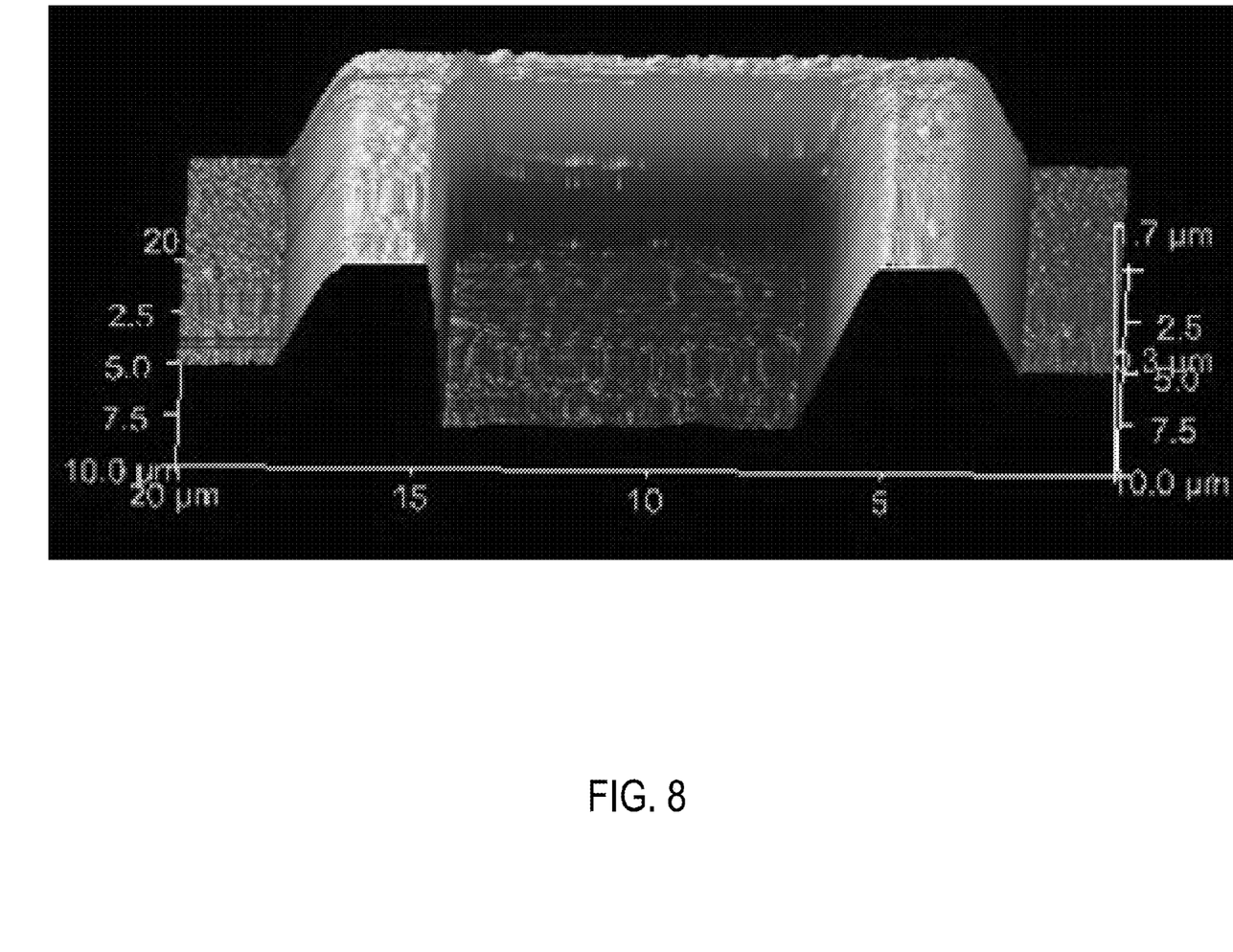
FIG. 8 illustrates atomic force microscopy (AFM) measurements of an actual interconnect via.

Referring now to FIG. 8, atomic force microscopy (AFM) measurements of an actual interconnect via are shown. In FIG. 8, the dimensions are shown in micrometers (μm). In FIG. 8, the angled sidewall having a sidewall angle of less than 90° is visible in the height profile of the passivation layer of the interconnect via.

Figure 9A:
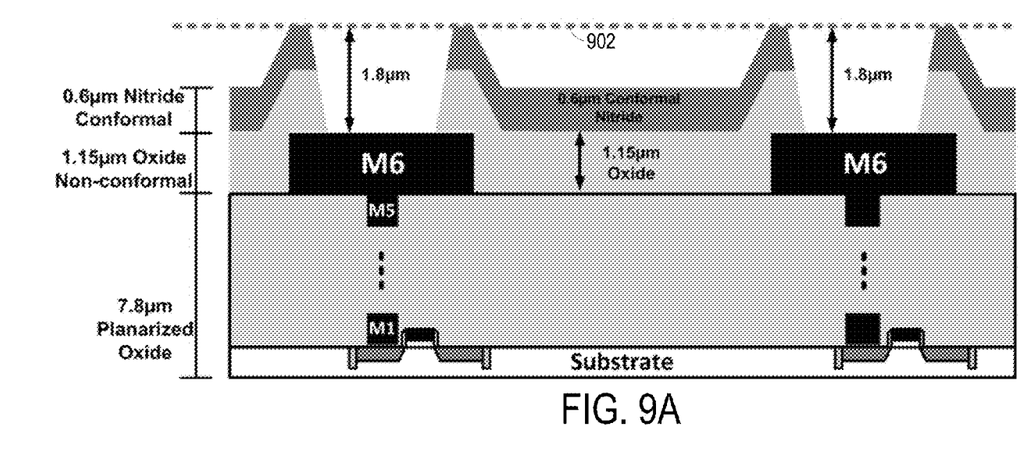
FIGS. 9A and 9B are cross-sectional schematic illustrations of the interconnect vias.
Figure 9B:
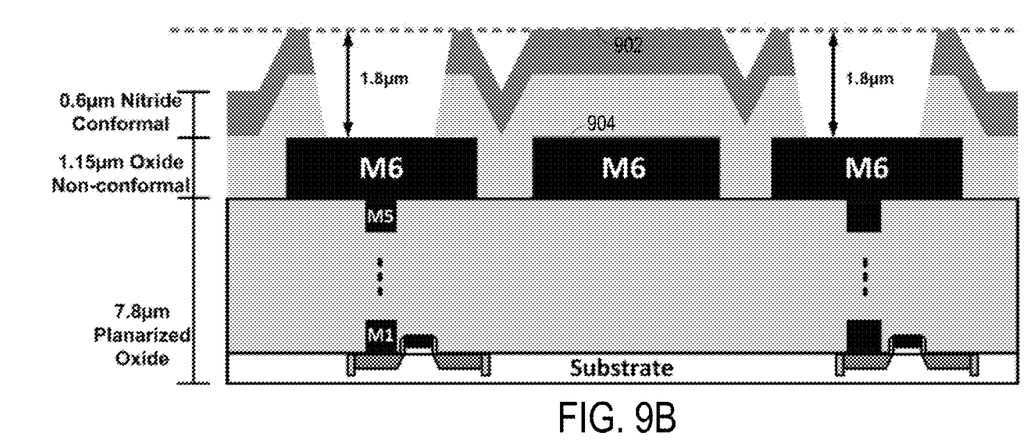

Referring now to FIGS. 9A and 9B, cross-sectional schematic illustrations of the interconnect vias are shown. In FIG. 9A, a surface plane 902 indicates the plane where the monolayer graphene channel is deposited. Because of the layout of the underlying metallization layers, including the M6 metallization layer, and the conformity of the subsequent oxide and nitride layers, the surface topography of the CMOS device may deviate from surface plane 902, as shown in FIG. 9A. As a result of the poor planarity, the post-CMOS processing steps described above may be subject to poor connection reliability and thus, poor overall yields, because the monolayer graphene and the subsequent electrical contacts may be disrupted. In FIG. 9B, a modified design for the interconnect via is illustrated including an additional metal pad 904 in the M6 metallization layer located between the interconnect vias. As a result of additional metal pad 904, the planarization of the surface of the CMOS device conforms better to surface plane 902, and the topography variation between the monolayer graphene channel and the electrical contacts to the interconnect vias is reduced. As a result, the overall yields for integration of monolayer graphene with a semiconductor device, as described herein, may be improved.

Figure 10:
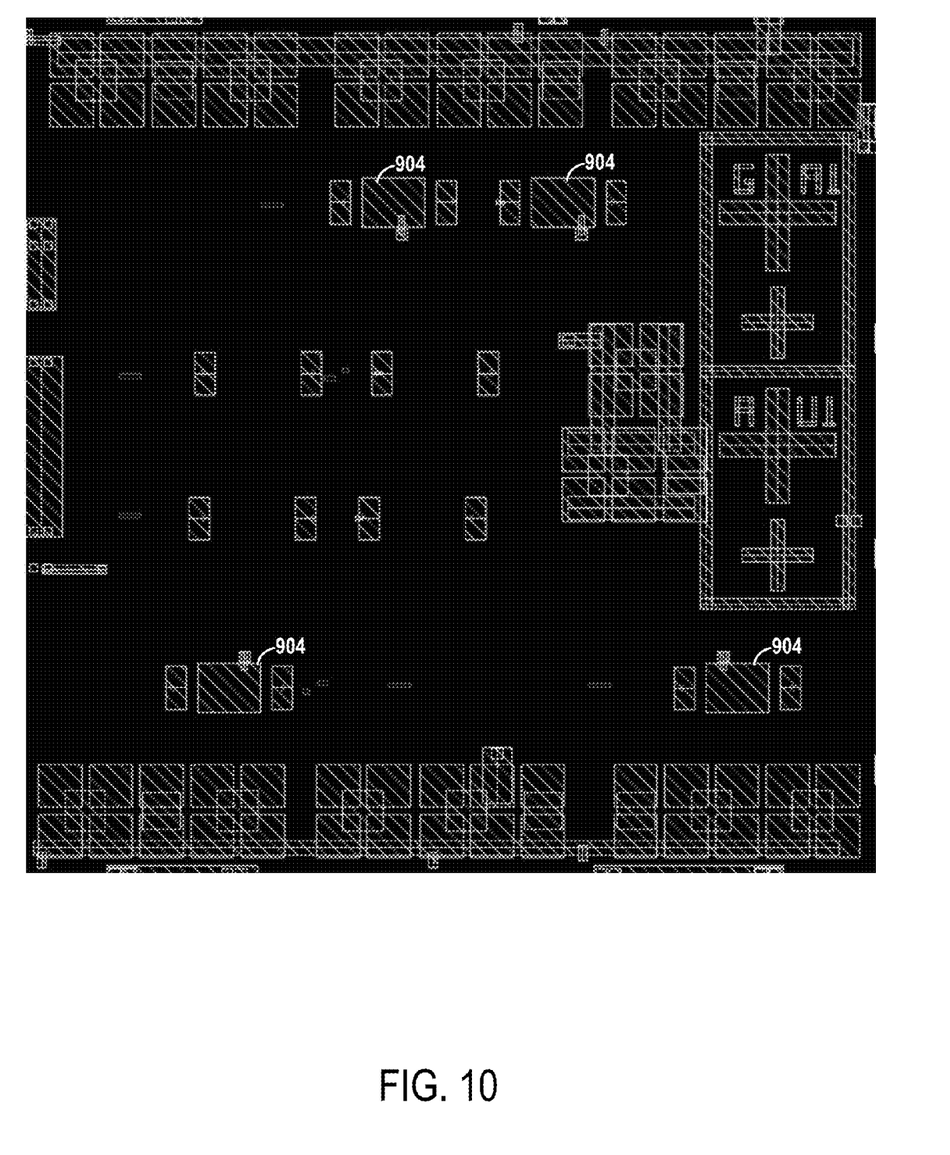
FIG. 10 is a layout mask image of the CMOS device prior to monolayer graphene transfer.

Referring now to FIG. 10, a layout mask image of the CMOS device prior to monolayer graphene transfer is shown. Specifically, FIG. 10 illustrates the layout mask image for the M6 metallization layer referenced previously. In particular, FIG. 10 shows the locations of additional metal pads 904 to improve planarization of the monolayer graphene surface topology, as described previously with respect to FIGS. 9A and 9B. It is noted that additional metal pads 904 may be added to all locations where the monolayer graphene channels are formed between interconnect vias, in various embodiments.

Figure 11:
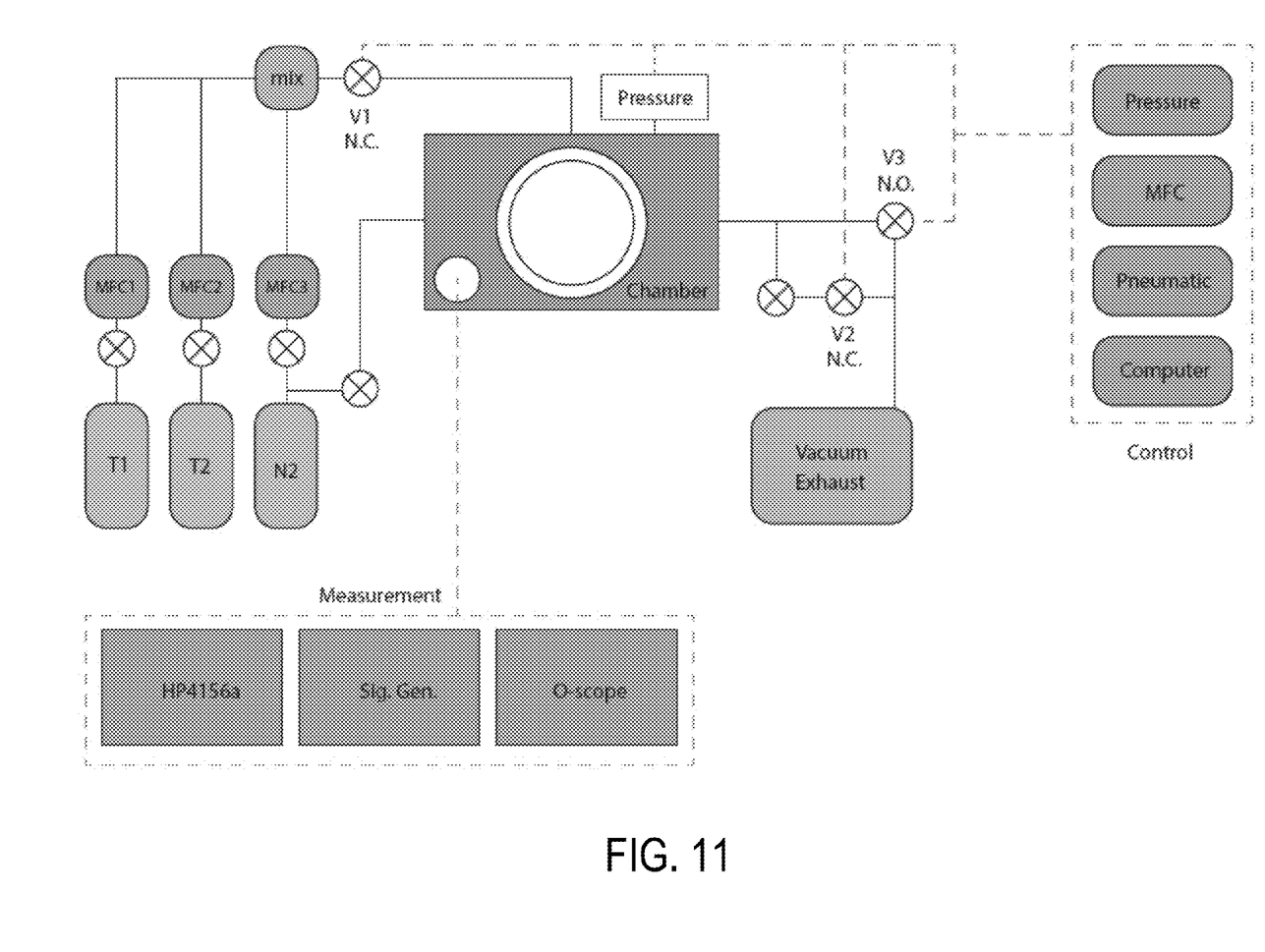
FIG. 11 illustrates selected elements of a block diagram of a measurement system for performing gas sensor tests.

Referring now to FIG. 11, selected elements of a block diagram of a measurement system for performing gas sensor tests is shown. The measurement system shown in FIG. 11 may be used to test the integrated monolayer graphene with a semiconductor device, as described herein. The measurement system includes a process chamber having a controlled atmosphere and accessible with test and measurement equipment. The controlled atmosphere may be a vacuum or a desired pressure and flow rate of one or more analyte gases, such as $NO_2$. Additionally, diluting gases such as $N_2$ and dried air may be employed in the controlled atmosphere. The measurements shown in FIGS. 6 and 12 may be performed using the measurement system shown in FIG. 11, which is a schematic diagram and is not drawn to scale.

Figure 12:
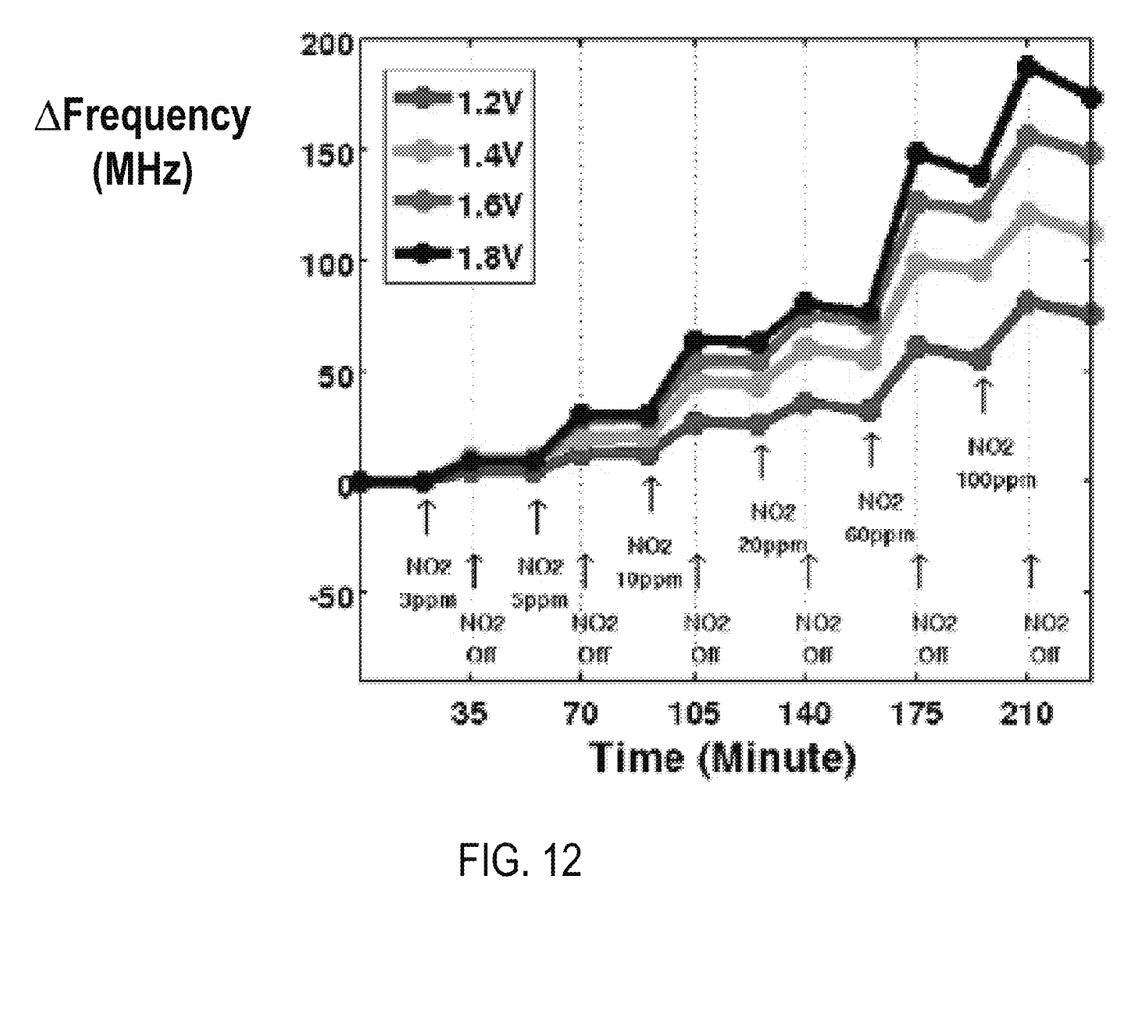
FIG. 12 illustrates data plots showing a frequency response of the CMOS device to exposure of varying concentrations of $NO_2$ for different supply voltages.

Referring now to FIG. 12, data plots showing a frequency response of the CMOS device to exposure of various concentrations of $NO_2$ for different supply voltages are shown. The measurement data shown in FIG. 12 were acquired using the CMOS device integrated with monolayer graphene, as described herein. As described previously with respect to FIG. 6, the ring oscillator circuit shown in FIG. 1 and included in the CMOS device generates a frequency output when a supply voltage is applied. In general, the output frequency of the ring oscillator circuit is directly proportional to the supply voltage. Furthermore, when the monolayer graphene channels in the CMOS device are exposed to $NO_2$, the resistance of the monolayer graphene decreases, resulting in an increase in the oscillation frequency. FIG. 12 illustrates data showing that the frequency response is directly related to $NO_2$ concentration for different supply voltages. Specifically, in FIG. 12, for each supply voltage (1.2V, 1.4V, 1.6V, 1.8V) an increase in the output frequency for increasing concentration of $NO_2$ gas (3 ppm, 5 ppm, 10 ppm, 20 ppm, 60 ppm, 100 ppm) is measured. In between each successive concentration, a measurement with no $NO_2$ ($NO_2$ off) was performed to recalibrate a baseline frequency, and it was observed that the frequency drops slightly in the intermediate absence of $NO_2$ exposure due to desorbing analyte.

In summary, the integration of monolayer graphene with a semiconductor device for gas sensing applications involves obtaining a CMOS device that is prepared to receive monolayer graphene channels. After population of the monolayer graphene channels on the CMOS device, electrical contacts are formed at each end of the monolayer graphene channels with interconnect vias having sidewalls angled at less then 90°. Additional metallization pads are added at the location of the monolayer graphene channels to improve planarity and reliability of the semiconductor processing involved.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method of preparing a gas sensor, the method comprising:
    transferring monolayer graphene to a top surface of a CMOS device comprising:
        forming a ring oscillator circuit;
        forming a passivation layer above the ring oscillator circuit that covers the top surface of the CMOS device; and
        forming interconnect vias comprising sidewalls through the passivation layer and establishing electrical connections to the ring oscillator circuit;
    patterning and etching the monolayer graphene to form monolayer graphene channels each having two ends in locations for electrically connecting the monolayer graphene channels to the interconnect vias at the top surface of the CMOS device; and
    electrically connecting each end of each of the monolayer graphene channels to one corresponding interconnect via per end.

2. The method of claim 1, wherein the interconnect vias have a sidewall angle of less than 90°.

3. The method of claim 1, wherein the CMOS device further comprises a metallic pad under the passivation layer at each of the locations underlying the monolayer graphene channels.

4. The method of claim 1, wherein transferring the monolayer graphene to the top surface of the CMOS device comprises chemical vapor deposition process for forming the monolayer graphene.

5. The method of claim 1, wherein patterning and etching the monolayer graphene to form the monolayer graphene channels comprises processes of electron beam lithography patterning and low-power reaction-ion-etching in oxygen plasma.

6. The method of claim 1, wherein electrically connecting each end of each of the monolayer graphene channels to the one corresponding interconnect via per end comprises depositing metal contacts.

7. The method of claim 6, wherein the metal contacts comprised of titanium (Ti) and/or gold (Au).

8. The method of claim 7, wherein the metal contacts comprised of a layer of Ti approximately 5 nm thick and a layer of Au approximately 45 nm thick.

9. The method of claim 1, wherein electrically connecting each end of each of the monolayer graphene channels to the one corresponding interconnect via per end comprises using electron beam lithography followed by metal deposition using e-beam evaporation and lift-off processes.

10. The method of claim 9, wherein the metal deposition comprises depositing titanium (Ti) and/or gold (Au).

11. The method of claim 10, wherein the depositing comprises depositing a layer of Ti approximately 5 nm thick and a layer of Au approximately 45 nm thick.

12. The method of claim 1, wherein electrically connecting each end of each of the monolayer graphene channels to the one corresponding interconnect via per end comprises depositing metal that spans from the end of the monolayer graphene to the interconnect via.

13. The method of claim 12, wherein electrically connecting each end of each of the monolayer graphene channels to the one corresponding interconnect via per end comprises depositing metal that spans from the end of the monolayer graphene to a metal pad in the interconnect via.

14. The method of claim 1, wherein the CMOS device further comprises a metallization layer beneath the passivation layer.

* * * * *